US00PP18100P2

(12) United States Plant Patent
Jonkers et al.

(10) Patent No.: US PP18,100 P2
(45) Date of Patent: Oct. 2, 2007

(54) ***IMPATIENS* PLANT NAMED 'SILTE PURSAR'**

(50) Latin Name: *Impatiens walleriana*
Varietal Denomination: Silte Pursar

(75) Inventors: Johanna B. Jonkers, Andijk (NL); Erik Smit, Enkhuizen (NL)

(73) Assignee: Goldsmith Seeds Europe B.V., Andijk (NL)

( * ) Notice: Subject to any disclaimer, the term of this patent is extended or adjusted under 35 U.S.C. 154(b) by 1 day.

(21) Appl. No.: 11/410,345

(22) Filed: Apr. 25, 2006

(51) Int. Cl.
*A01H 5/00* (2006.01)

(52) U.S. Cl. ..... Plt./317
(58) Field of Classification Search ..... Plt./317
See application file for complete search history.

*Primary Examiner*—Kent Bell
(74) *Attorney, Agent, or Firm*—Jondle & Associates P.C.

(57) ABSTRACT

A new *Impatiens* plant particularly distinguished by medium-sized, bi-colored purple and white, rose-shaped flowers borne well above the foliage, deep-green foliage with ovate leaves, an early flowering response, floriferous throughout the summer, and a medium-sized, round and bushy plant habit, is disclosed.

1 Drawing Sheet

Genus and species: *Impatiens walleriana.*
Variety denomination: 'Silte Pursar'.

BACKGROUND OF THE NEW PLANT

The present invention comprises a new and distinct cultivar of *Impatiens*, botanically known as *Impatiens walleriana,* and hereinafter referred to by the cultivar name 'Silte Pursar'. The new cultivar originated from a hybridization made in May 2003 in Andijk, The Netherlands. The female parent was the proprietary salmon-star-flowered *Impatiens* plant 'ID03-30-10' (unpatented), while the male parent was the proprietary red-star-flowered *Impatiens* plant 'ID03-19-13' (unpatented). The seeds produced by the hybridization were sown in Andijk, The Netherlands in October 2003. A single plant selection was chosen for further evaluation and for asexual propagation in December 2003 in Andijk, The Netherlands.

The new cultivar was created in 2003 in Andijk, The Netherlands and has been asexually reproduced repeatedly by vegetative cuttings and tissue culture in Andijk, The Netherlands and Hillscheid, Germany over a two-year period. 'Silte Pursar' has not been observed under all possible environmental conditions. The present invention has been found to retain its distinctive characteristics through successive asexual propagations.

Plant Breeder's Rights for this cultivar were applied for in Canada on Oct. 17, 2005 and with the European Union on Nov. 18, 2005.

SUMMARY OF THE INVENTION

The following are the most outstanding and distinguishing characteristics of this new cultivar when grown under normal horticultural practices in Andijk, The Netherlands, and Hillscheid, Germany.

1. Medium-size, double-type, bi-colored purple and white flowers borne well-above the foliage;
2. Deep green foliage with ovate leaves;
3. A medium-sized, round and bushy plant habit;
4. An early flowering response; and
5. Floriferous throughout the summer.

DESCRIPTION OF PHOTOGRAPH

This new *Impatiens* plant is illustrated by the accompanying photograph which shows overall plant habit including blooms, buds, and foliage of the plant; the colors shown are as true as can be reasonably obtained by conventional photographic procedures. The photograph is a close-up of a portion of a 10-week old plant, grown in a greenhouse in Hillscheid, Germany in late May 2005.

DESCRIPTION OF THE NEW CULTIVAR

The following detailed descriptions set forth the distinctive characteristics of 'Silte Pursar'. The data which defines these characteristics were collected from asexual reproductions carried out in Hillscheid, Germany. The plant history was taken in mid September on 9- to 10-week old un-pinched plants which had been planted as rooted cuttings in 12-cm pots in mid-July 2005 and grown in a greenhouse at a minimum temperature of 21° C. Color readings were taken under natural light in the greenhouse. Color references are primarily to The R.H.S. Colour Chart of The Royal Horticultural Society of London (R.H.S.) (2001).

DETAILED BOTANICAL DESCRIPTION OF THE NEW PLANT

Classification:
*Family.*—Balsaminaceae.
*Botanical.*—*Impatiens walleriana* Hook.
*Common name.*—*Impatiens.*

Parentage:
*Female parent.*—'ID03-30-10' a proprietary salmon-star, bi-color-flowered *Impatiens* plant (unpatented).
*Male parent.*—'ID03-19-13' a proprietary red-star, bi-color-flowered *Impatiens* plant (unpatented).

Growth:
*Growth and branching habit.*—A medium-sized, round, bushy, and well-branched plant habit; the growth is indeterminate and weak after the beginning of flowering.
*Height.*—14.0 cm.
*Width.*—10.5 cm.

*Propagation.*—Terminal tips for cuttings.
*Time to produce a finished flowering plant.*—8 weeks for a 12-cm pot.
*Time to initiate and develop roots.*—18 days or less at 22° C.

Branches:
*Average number.*—4 to 6.
*Length of branches.*—9 cm to 13 cm.
*Internode length.*—About 4 cm to 5 cm.
*Diameter of branches* (*at midpoint*).—0.6 cm to 0.7 cm.
*Stem color.*—Mainly RHS 145C (pale green); a weak infusion of anthocyanin, RHS 185D, may occur at the stem base.

Leaves:
*Arrangement.*—Mostly alternate.
*Size.*—Length: 6.5 cm. Width: 4.3 cm.
*Shape.*—Broadly elliptical to nearly round or rhomboid.
*Apex.*—Acuminate.
*Base.*—Acute.
*Margin.*—Weakly crenate, ciliate (few).
*Color* (*mature leaves*).—Upper surface: RHS 137B. Lower surface: RHS 138B with patches of RHS 186C (dull purple).
*Color* (*immature leaves*).—Upper surface: Near RHS 137A. Lower surface: RHS 138B, with weak patches of RHS 186C (dull purple).
*Texture.*—Glabrous.
*Venation color.*—Upper surface: RHS 145C (pale green) and hardly visible. Lower surface: RHS 145B.
*Petioles.*—Length: About 2.0 cm to 3.0 cm. Diameter: 0.3 cm. Color: Upper surface: RHS 145C. Lower surface: RHS 145B. Texture: Glabrous.

Flower buds:
*Shape.*—Ovoid to round.
*Size.*—Length: 1.5 cm. Diameter: 1.3 cm.
*Color at tight bud.*—RHS 71D.

Inflorescence:
*Blooming habit.*—8 weeks after planting of rooted cuttings.
*Inflorescence type.*—Inflorescences appear solitary in the leaf axils of the upper nodes of the stems.
*Number of flowers per inflorescence.*—2 to 4 in various stages of development.
*Flowering season.*—Continuously flowers, mainly from March to October, depending on light intensity.
*Lastingness of the individual blooms on the plant.*—About 5 to 7 days (at 18° C. in a greenhouse in the spring).
*Fragrance.*—None.
*Peduncle.*—Color: RHS 146C. Size: Length: Up to 8.0 cm. Diameter: 0.25 cm near the base. Texture: Flexible, glabrous.

Flowers:
*Form of corolla.*—Double-type.
*Shape of corolla.*—Rose-shaped at opening, round outline; later the outer petals open very wide and are horizontally directed, while the inner petals remain more or less upright.
*Corolla size.*—Diameter: 3.4 cm to 3.8 cm. Depth: 1.7 cm.
*Number of petals.*—About 18 to 20.

Petals:
*Shape.*—Obovate; largest petal is cordate.
*Apex.*—Rounded; largest petal is emarginate.
*Base.*—Attenuate.
*Margin.*—Entire.
*Size.*—Length: 1.8 cm to 2.1 cm. Width: Mostly 1.7 cm to 1.8 cm; largest petal is 2.2 cm.
*Color.*—General: Bi-colored purple and white. Upper surface: RHS 74A (purple). Lower surface: RHS 71B. Markings: RHS 155D (white) at the basal and middle part of the petals.
*Petal texture.*—Smooth, satiny.

Spur:
*Shape.*—Curved, downward directed.
*Color.*—RHS 146C.
*Size.*—Length: Up to 3.3 cm. Diameter: 0.2 cm at the flower end.

Reproductive organs:
*Stamens.*—Usually no stamens.
*Pistils.*—Style and stigma: Not developed. Ovary: 5-celled. Ovary length: About 0.6 cm. Ovary color: RHS 143B (green).

Fruit and seed set: No seed set observed.

Disease and insect resistance: No particular resistance or susceptibility has been observed.

COMPARISON WITH PARENTAL AND COMMERCIAL CULTIVARS

'Silte Pursar' differs from the female parent 'ID03-30-10' (unpatented) by having purple and white, double-type flowers, while 'ID03-30-10' has salmon-star, single flowers.

'Silte Pursar' differs from the male parent, 'ID03-19-13' (unpatented), by having purple and white, double-type flowers, while 'ID03-19-13' has red-star, single flowers.

'Silte Pursar' differs from the commercial cultivar 'TiPar' (U.S. Plant Pat. No. 12,544) in that 'Silte Pursar' has shorter leaves and a more compact plant habit than 'TiPar'. Additionally, 'Silte Pursar' has fewer petals and is more floriferous during the summer than 'TiPar'.

I claim:

1. A new and distinct cultivar of *Impatiens* plant as shown and described herein.

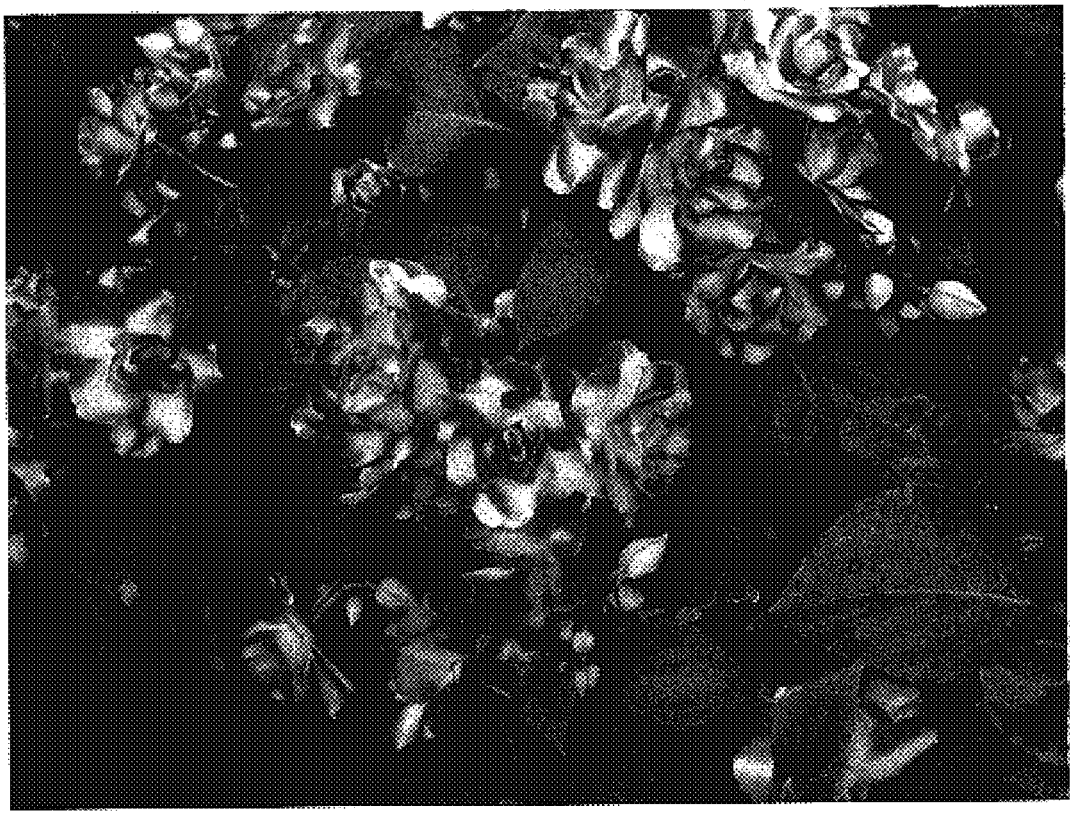

* * * * *